Figure 1:
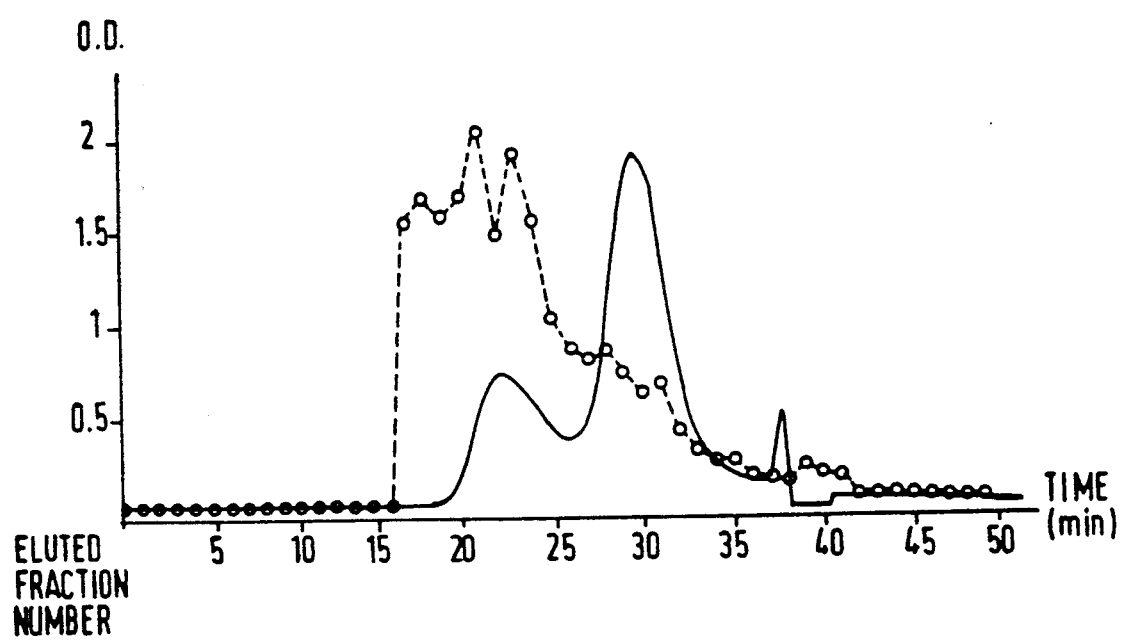

United States Patent [19]

Khayat et al.

[11] Patent Number: 5,219,728
[45] Date of Patent: Jun. 15, 1993

[54] SOLUBLE FORMS OF LOW AFFINITY FC GAMMA RECEPTORS, PROCESS FOR THEIR IDENTIFICATION AND DOSAGE, A CORRESPONDING DOSAGE KIT, AND APPLICATIONS

[75] Inventors: David Khayat, Paris, France; Jay Unkeless, Brooklyn, N.Y.; Claude Jacquillat, Paris, France

[73] Assignee: Universite Pierre Et Maire Curie, Paris, France

[21] Appl. No.: 353,676
[22] PCT Filed: Feb. 23, 1988
[86] PCT No.: PCT/FR88/00103
§ 371 Date: Apr. 7, 1989
§ 102(e) Date: Apr. 7, 1989
[87] PCT Pub. No.: WO88/06733
PCT Pub. Date: Sep. 7, 1988

[30] Foreign Application Priority Data
Feb. 24, 1987 [FR] France ................................ 87 02400

[51] Int. Cl.$^5$ ..................... C12Q 1/00; G01N 33/53; A61K 35/14; A61K 37/00; A61K 37/10; A61K 37/04; A01N 37/18; C07K 3/00
[52] U.S. Cl. ..................................... 435/7.2; 530/380; 530/395; 435/7.9; 435/7.92; 435/7.94; 435/7.95; 514/2; 514/8
[58] Field of Search .......................... 435/7, 9, 7.1, 7.2, 435/7.9, 7.92, 7.94, 7.95; 530/380, 395; 514/2.8

[56] References Cited

FOREIGN PATENT DOCUMENTS 0119736 9/1984 European Pat. Off. .
0125893 11/1984 European Pat. Off. .
86/04421 7/1986 World Int. Prop. O. .

OTHER PUBLICATIONS

Fleit et al (1982) Human neotrophil Fc γreceptor . . . PNAS 79:3275-3279.
Ruan et al (1984) Abstract only CA 103:35728 The Immune Detection . . . .
Khayat et al (1984) Circulatory Cell Free Fc γ2b/γ1 . . . . J Immunol 132:2496-2501.
Fleit et al., "Identification of a Soluble Form of a Human . . . ", *J. leukocyte Biol.* vol. 40 (3) p. 252 (1986).
Ulvestad et al., "Soluble Fc γ Receptors (FcR) in Human Sera . . . ", *Scandonovian J. of Immunology* vol. 24(4) p. 481 (1986).
Pure et al., "Identification of Soluble Fc Receptors . . . ", *J. Exp. Med* vol. 160, pp. 1836-1849 (1984).
Perussia et al, "The Fc Receptor for IgG on Human . . . ", The Journal of Immunology, vol 133, No. 1, pp. 180-188 (1984).
Khayat et al, "Soluble circulating Fc gamma receptors . . . " Journal of Immunological, Methods, vol. 100, Jun. 26, 1987 pp. 235-241.
Looney et al, "Humman monoytes and U937 Cells . . . " Journal of Immunology, vol. 136 No. 5 1986.
Anderson et al, "Monoclord antibodies to Fc receptors . . . ", Chem. Abstracts, vol. 261 (27), 12856-64, 1986.
Fleit et al, "Identification of a soluble . . . ", Biological Abstracts vol. 40, No. 3, p. 252 1987.
Pure et al., "Identification of soluble Fc receptors . . . ", Chem. Abstracts, vol. 102, No. 11 (1985).
Rosenberg et al, "Fc receptors for IgG . . . ", Chem Abstracts vol. 103, No. 17 (1985).

*Primary Examiner*—Christine M. Nucker
*Assistant Examiner*—David R. Preston
*Attorney, Agent, or Firm*—Jacobson, Price, Holman & Stern

[57] ABSTRACT

Receptors, characterized by the fact that they consist of the product obtained by affinity chromatography on a column coupled with 3 G8 antibodies or lectins or polyclonal anti-receptor FcR antibodies of a biological fluid of human origin, then by gel permeation. The spectrum of said product, electrophoresis acrylamide gel in reducing condition, comprising a major band corresponding to a molecular mass of between 72000 and 76000 daltons, and a number of minor bands. According to its purified form, the receptor consists of a glycoprotein with a molecular mass of between 72000 and 76000 daltons, recognized by ELISA and Western Blotting by the monoclonal anti-Leu 11b antibody. Application of said receptors to diagnosis and to follow-up treatment of diseases involving Fc receptors (infectious diseases, diseases of the autoimmune system, rejection of transplants, cancer and myeloma and AIDS), as well as to the study of human polymorphisms.

24 Claims, 4 Drawing Sheets

EXPLANATION OF THE TEST

Lymphokine sought assayed specifically by the test

SOLUBLE FORMS OF LOW AFFINITY FC GAMMA RECEPTORS, PROCESS FOR THEIR IDENTIFICATION AND DOSAGE, A CORRESPONDING DOSAGE KIT, AND APPLICATIONS

The present invention relates to soluble forms of low affinity receptors for the Fc fragment of IgG molecules; the present invention also relates to a method for the identification and assay of soluble forms of low affinity Fc gamma receptors, especially human soluble Fc receptors; it also relates to a kit of the reagents necessary for carrying out this method; it relates finally to the applications of this method for the diagnosis of pathological conditions in which the above-mentioned receptors are involved, such as infectious diseases, autoimmune diseases, transplant rejections, human complex diseases, cancers, myelomas and acquired immune deficiency syndrome (AIDS), for the therapeutic monitoring of the course of these conditions, as well as for the study of human polymorphisms.

At the surface of many cells, in particular the cells of the immune system (macrophages, B lymphocytes, polymorphonuclear leukocytes, NK cells, and the like), there are receptors which permit a relationship between antibodies or immunoglobulins and these cells are involved in immunity. These receptors have an affinity for the Fc fragment of antibodies (FcR). This Fc fragment corresponds to the portion of immunoglobulins not endowed with antibody activity. The importance of these receptors is considerable, since their mediation makes possible the recognition of foreign antigens (viruses, tumor cells and the like) and the initiation of a cytotoxic reaction, by T lymphocytes or humoral, with secretion of specific antibodies by B lymphocytes; phagocytosis, that is to say the extraction from tissues and the blood of particles recognized as foreign by the cells of the reticuloendothelial system (monocytes, macrophages); cell interactions between different cells involved in immunity; the transplacental transfer of antibodies from mother to fetus; and the clearance of immune complexes whose pathogenic role in many conditions is known.

The existence of a secretion of these receptors for the Fc fragment (FcR) by mouse T cell cultures activated by a specific activator has been demonstrated. These Fc receptor molecules, secreted in vitro under very special conditions of activation and culture (in particular, in medium devoid of all serum, which has a deleterious effect on the cells in culture), still possess the capacity to bind immunoglobulins through their Fc fragment, and they have hence been christened "immunoglobulin binding factor" (IBF). The existence of this type of IBF has been demonstrated for three classes of immunoglobulins, IgG, IgA and IgE, namely the factors IgGBF, IgABF and IgEBF.

It has, moreover, been demonstrated that these IBF molecules are capable, when they are in contact with B lymphocytes in culture, or even myeloma cells in vitro, of completely inhibiting the activation of these cells and, as a result, the secretion of immunoglobulins by these B or myeloma cells. The molecules in question are hence secreted by cells belonging to the immune system under artificial conditions of in vitro culture, but are nevertheless endowed with a functional capacity to bind antibodies and to bring about a substantial suppression of the activation of the B lymphocyte system (lymphokine).

The existence of an Fc receptor for mouse IgG immunoglobulins (FcR) in mouse serum has been demonstrated. These molecules have been defined both by their capacity to be recognized by a monoclonal antibody specific for mouse Fc gamma receptors (monoclonal antibody 2.4G2) and their functional capacity to be purified from immunoglobulin Fc fragments. This discovery is extremely important, since this lymphokine is secreted at a level which increases with age (level zero at birth, appearing at around the fifth day in newborn mice and becoming systematically detectable at around the seventh day), that this level increases in proportion to the presence of infections or, more generally, that the immune system is stimulated (mice kept in a microbe-free environment having strictly zero levels throughout their life), this level being, moreover, determined in a relative manner by genetic factors within a population of homozygotic mice.

In addition, the existence has now been discovered, in particular in human serum, of a lymphokine having the capacity to bind to the Fc fragments of immunoglobulin, namely the circulating soluble serum form of low affinity Fc gamma receptors, also designated by the abbreviation Fc-gamma RLo, or alternatively "CD16".

These receptors are present in biological fluids (in particular serum) in polymerized form, as could be observed by molecular weight measurements which, for example, yielded a value above approximately 700,000 for the glycoprotein which has been shown to have a molecular weight in the monomer state of 72,000 to 76,000.

The subject of the present invention is a low affinity, soluble Fc γ R type III receptor (or CD16), consisting of a glycoprotein of molecular mass 72,000-76,000 daltons which is recognized in ELISA and Western Blotting by the monoclonal antibody anti-Leu 11b.

The subject of the invention is also a low affinity, soluble Fc γ R type III receptor (or CD16), which consists of the product obtained by affinity chromatography, on a column coupled to 3G8 antibodies or to lectins (for example Lens Culinaris Agglutinin (LCA), wheatgerm agglutinin or concanavalin) or to anti-FcR receptor polyclonal antibodies, of a biological fluid of human origin, followed by gel filtration, the spectrum of the said product, in acrylamide gel electrophoresis under reducing conditions, containing a major band corresponding to a molecular mass of between 72,000 and 76,000 daltons and a plurality of minor bands, of which the main ones correspond to molecular masses, respectively, of:

between 64,000 and 68,000 daltons
between 51,000 and 55,000 daltons
between 42,000 and 46,000 daltons
between 33,000 and 37,000 daltons.

The invention also relates to an Fc γ R type III receptor essentially comprising the fraction of molecular mass 33,000-37,000 daltons, as appears in acrylamide gel electrophoresis in the presence of a reducing agent and a detergent agent such as sodium dodecyl sulfate (SDS).

The biological fluids to which the present invention relates are, inter alia, serum and plasma fluids, cephalorachidian fluids, urines and ascitic fluids.

A feature of all these receptors which may be mentioned is that, in the Dot Blot technique, they recognize a rabbit anti-FcR receptor polyclonal antibody.

The invention finally relates to each of the fractions of the Fc γ R type III receptor, as are defined above, as well as to all possible combinations of these fractions.

The present invention also relates to a method for the identification, detection or assay of these lymphokines having the capacity to bind to the Fc fragments of immunoglobulin, in particular the human serum soluble Fc receptor.

The method according to the present invention for the identification or assay of soluble forms of the low affinity Fc γ R type III receptor (or CD16) consists in:

(a) binding, to a solid phase, a first antibody, which is a monoclonal or polyclonal antibody or alternatively a fraction of a monoclonal or polyclonal antibody (for example a Fab fragment), directed against a conformational epitope of the Fc γ receptor to be identified or assayed;

(b) washing the said solid phase to remove the said first antibody which is not coupled;

(c) incubating the sample containing the Fc γ receptor to be assayed in the presence of the solid phase coated with the said first antibody;

(d) washing to remove the material not specifically bound to the said first antibody;

(e) incubating, in the presence of the resulting solid phase, a second antibody, which is a monoclonal or polyclonal antibody, or alternatively a fraction of a monoclonal or polyclonal antibody (for example a Fab fragment), and which is an anti-Fc receptor recognizing the same category of Fc receptors as the first antibody, but by a completely different epitope;

(f) washing to remove the said second antibody not specifically bound;

(g) incubating, in the presence of the resulting solid phase, a third antibody, which is an antibody capable of specifically recognizing the said second antibody;

(h) washing to remove the third antibody not specifically bound; and (i) assaying the third antibody bound, and deducing therefrom the quantity of Fc receptor initially present in the sample.

In the stage (a), the monoclonal antibody 3G8 is used, in particular, as the first antibody. In the stage (e), a mouse IgM consisting of the monoclonal antibody anti-Leu 11b is used, in particular, as the second antibody. In the stage (g), a polyclonal antibody, namely a goat anti-mouse IgM antibody, is used as the third antibody.

According to an especially preferred embodiment of the method according to the invention, in the stage (g), a third antibody labeled with an enzyme is employed and, in the stage (i), a colorimetric substrate for the said enzyme is added and, after the colorimetric reaction has been stopped, for example by adding aqueous sulfuric acid solution, the colorimetric change is read, from which the quantity of Fc receptor sought is deduced. In effect, the colorimetric change is proportional to the quantity of the third antibody and, as a result, proportional to the quantity of second antibody, and hence of Fc receptor initially present in the sample.

Preferably, the enzyme is peroxidase, in particular horseradish peroxidase, and the colorimetric substrate for peroxidase is ortho-phenylenediamine, in the presence of hydrogen peroxide, the colorimetric reading being performed at 492 nm.

The incubation of the stage (a), for the binding of the first antibody to the solid phase, is performed, for example, at a temperature of the order of 4° C., for a period of time ranging from 8 to 12 hours.

As regards the incubations of the stages (c), (e) and (g), these are performed, in particular, at room temperature, over a period of time ranging from 1 to 4 hours.

Figure 7A:
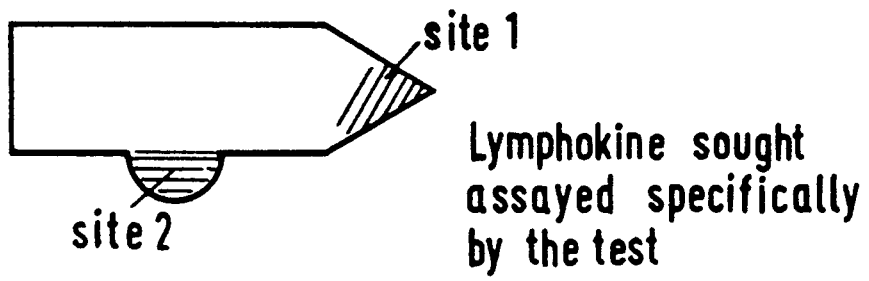
Figure 7B:
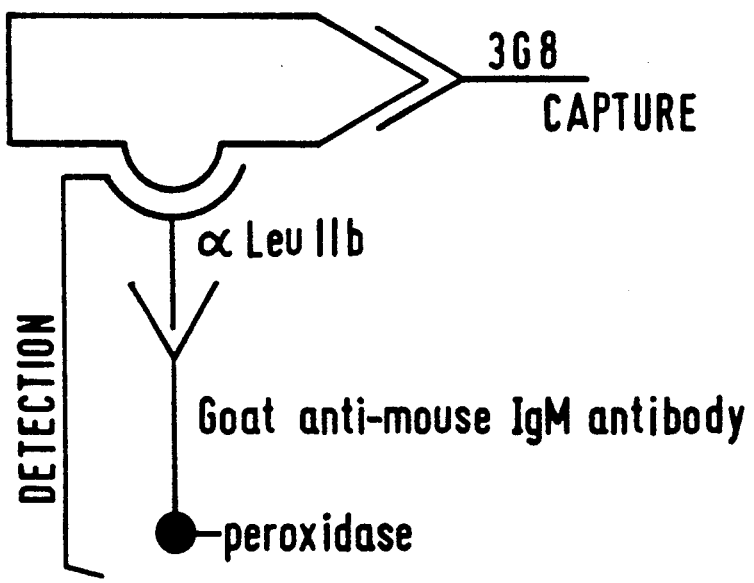

FIG. 7 of the attached drawing explains the assay according to the invention. The lymphokine sought, which is assayed specifically by this method, contains a first site of capture by the first antibody (3G8), and a second site of detection by the sequence αLeu 11b-goat anti-mouse IgM antibody and peroxidase.

The subject of the present invention is also the kit of the reagents necessary for carrying out this method, this kit comprising:

a solid support, in particular a microtitration plate, provided with a first antibody which is a monoclonal or polyclonal antibody, or alternatively a fraction of a monoclonal or polyclonal antibody, and which is directed against a conformational epitope of the Fc γ receptor to be assayed;

a second antibody, which is a monoclonal or polyclonal antibody, or alternatively a fraction of a monoclonal or polyclonal antibody, and which is an anti-Fc receptor recognizing the same category of Fc receptors as the first antibody, but by a completely different epitope;

a third antibody, which is an antibody capable of specifically recognizing the second antibody; and a system for assay of said third antibody.

These three antibodies, as well as a system for assay of the third antibody, have been defined above.

As a detector of background, that is to say as a negative control, xenogenic sera (fetal calf, horse, goat) are used.

As a standard enabling provision to be made for a qualitative positive control of the method, a positive known serum is used, and, in order to be able to quantify the method, an extract of human polymorphonuclear leukocytes are used. These polymorphonuclear leukocytes are purified according to classical purification techniques, are counted and are then lysed with a mild detergent which does not destroy the conformational structures of the polymorphonuclear cell receptors, which would no longer be able to be recognized subsequently during the test with the 3G8 antibody, and, knowing the number of Fc receptors per polymorphonuclear cell, the number of polymorphonuclear cells at the start and the different dilutions at which these polymorphonuclear cells are tested, it is possible, by a simple relationship, to determine the correspondence between the soluble Fc receptors in the sera tested and a theoretical number of Fc receptors of polymorphonuclear cells detected in the cell lysate. A lysate, purified according to classical techniques, of human polymorphonuclear cells, lysed exclusively with an aqueous solution of 30 mM octylthio beta-d-glucoside + 5 mM DFP at 4° C.

The applications of this method are essentially diagnostic applications and applications for monitoring the therapeutic use of these lymphokines. The latter are, in effect, substances, the variations of which are linked to the fine activation of the B lymphocyte system and/or tho macrophage system and whose variation in level enables the state of stimulation of this system to be determined. This is of major importance in infectious diseases, autoimmune diseases, transplant rejections, cancers and myelomas, and acquired immune deficiency syndrome (AIDS). Moreover, after injection of the lymphokine (human Fc receptor), it is possible, by means of this test, to assay the variations in the serum levels and, as a result, to manage more effectively and with less toxicity the therapeutic capabilities of this lymphokine in human medicine. In effect, such a lymphokine is capable, like its in vitro homolog, of specifically inhibiting the secretion of an immunoglobulin class and hence of halting an effector mechanism in some pathological conditions, such as the abovementioned diseases, without thereby, as a result of its specificity—in effect, a receptor for IgG will bring about the inhibition of only IgG secretion—bringing about an inhibition of the secretion of the other immunoglobulin classes, hence enabling a resultant immunosuppression of the patient to be avoided.

Likewise, by blocking the Fc fragments of immunoglobulins already engaged in an adverse antigen-antibody reaction (as in the case of antiplatelet autoantibodies in idiopathic thrombocytopenic purpura, for example), this lymphokine may prevent the relationship between these immune complexes and the cells of the reticuloendothelial system which would normally have phagocytosed these antigens (platelets in the case of idiopathic thrombocytopenic purpura), leading to the pathogenic effect (thrombocytopenia in the chosen example).

The invention also relates to a medicinal product containing an Fc γ R type III receptor or at least one fraction which is a constituent thereof, as are defined above.

A particular embodiment of the assay method of the invention will be described below.

(1) Preparation of the Microtitration Plates

The microtitration plates used are 96-well U-bottomed poly(vinyl) chloride plates (manufactured by Société "Dynatech").

The monoclonal antibody 3G8 is introduced, on the basis of 3 μg per well, in 100 μl of carbonate buffer at pH 9.6. The incubation lasts 8 to 12 hours at a temperature of 4° C.

(2) Washing

The plates are washed 6 times with PBS (Phosphate Buffered Saline) containing 0.1% v/v of Tween 20. This washing solution, which will be used again in subsequent stages of this assay, will now be designated more simply by the term "PBS Tween".

(3) Deposition of the Sample to be Assayed

100 μl of the sample to be assayed, pure or diluted in PBS Tween which has been left for 4 hours at approximately 22° C. (room temperature), are deposited in each well.

(4) Washing

This washing is performed in the same manner as in the stage (2).

(5) Deposition of Anti-Leu-11b Antibody 80 ng of anti-Leu-11b antibody (source: Beckton-Dickinson), diluted in 100 μl of PBS Tween, are deposited in each well. Incubation is performed for 2 hours at approximately 22° C.

(6) Washing

This washing is performed in the same manner as in the stage (2).

(7) Deposition of Goat Anti-mouse IgM Antibody Conjugated to Horseradish Peroxidase The abovementioned antibody (source: Jackson Immuno-Research Laboratories Inc.), diluted to 1/5,000 in PBS Tween producing in total 100 μl per well, is introduced. Incubation is performed for 1 hour at 22° C.

(8) Washing

This washing is performed in the same manner as in the stage (2).

(9) Deposition of the Colorimetric Substrate for Peroxidase

150 μl per well of citrate phosphate buffer containing 4 mg/ml of ortho-phenylenediamine and 0.8 μl/ml of hydrogen peroxide are deposited.

The colorimetric reaction is stopped by depositing 75 μl per well of 10% aqueous sulfuric acid solution, and the result is read at 492 nm in an ELISA reading apparatus.

By means of the assay method according to the present invention, a molecule corresponding to a soluble serum form of the low affinity receptor for the Fc fragment of IgG has been demonstrated in human blood.

The characterization of the Fc γ R type III receptors of the invention will now be described.

A normal human serum (68 ml) is passed, in a first stage, through a column of Sepharose coupled to 3G8 monoclonal antibodies (2 mg of 3G8 antibody per ml of Sepharose; total column volume: 1 ml), at room temperature. This column is then washed using 150 ml of a 0.1% strength solution of "Tween 20" in phosphate buffered saline solution, and the material adsorbed is then eluted using ½M acetic acid solution, the fragments having a volume of 0.5 ml. These fractions are immediately neutralized using 3M sodium bicarbonate solution. The serum, before and after affinity chromatography, as well as the elution fractions, are tested for their content of soluble low affinity type III Fc receptor. The fractions which show immunological activity are then combined, and 0.2 ml of this pool of fractions is subjected to gel filtration on a column of volume 25 ml of "Superose 6" (Pharmacia); this "Superose 6" column is equilibrated in 50 mM ammonium bicarbonate solution at pH 8. The fractions having a volume of 0.5 ml are collected and tested using a direct ELISA assay method. This ELISA method consists in testing the elution fractions without passing through the stage of capture using the monoclonal antibody 3G8. These fractions are affixed directly to a solid support of the 96-well PVC plate type, and are then, after washing, reacted with the monoclonal antibody anti-Leu 11b, followed, after 2 hours, by a second anti-mouse IgM antibody labeled with peroxidase.

FIG. 1 of the attached drawing shows the results of this second stage of the purification, hence corresponding to the gel filtration. Two curves are seen in this figure. The elution fraction numbers, as well as the time elapsed (expressed in minutes) are plotted as abscissae, and the optical density as seen on the reading of the wells in the direct ELISA method is plotted as ordinates. The curve in the form of a continuous line corresponds to the elution chromatogram of this gel filtration, and gives only the quantity of proteins without giving their characteristics. The second curve (○—○) represents the immunoreactivity of each of the elution fractions, in terms of purified soluble Fc receptor. It is hence observed that the peak between the fractions 20 and 25 bears virtually the whole of the purified soluble Fc type III receptor type immunoreactivity.

Figure 2:
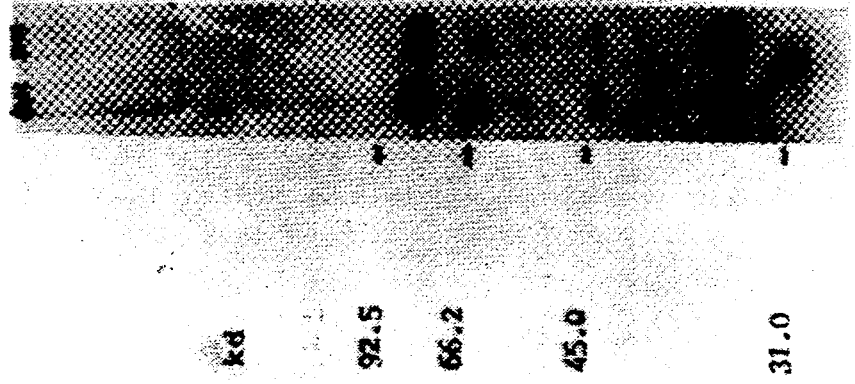

The fractions 20 and 22, which are the richest in soluble Fc receptor type immunoreactivity since the optical density rises to around 2 units, were lyophilized, and they were subjected to acrylamide gel electrophoresis in the presence of SDS and a reducing agent. These fractions are shown in FIG. 2, and show the existence of a characteristic principal major band whose molecular weight is 72,000 to 76,000 daltons, but also bands of somewhat minor importance at around 66,000, 3,000, 43,000 and 35,000 daltons.

Figure 3:
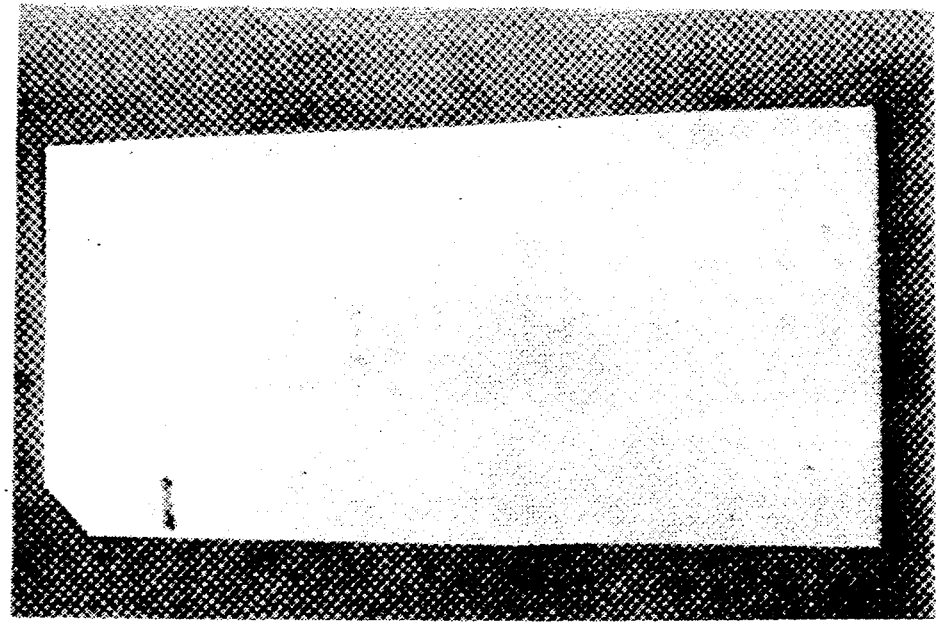

These bands are then transferred by horizontal flow onto a nitrocellulose filter, according to the technique known as "Western Blotting"; this cellulose nitrate paper is then reacted with the monoclonal antibody anti-Leu 11b and, after washing, this cellulose nitrate filter is reacted with anti-mouse IgM polyclonal antibody labeled with alkaline phosphatase. This is shown in FIG. 3. It is found that only one of these bands actually reacts in the Western Blotting technique, and is hence still recognized by the anti-Leu 11b antibody; it is the major band at 72,000–76,000 daltons.

Figure 4:
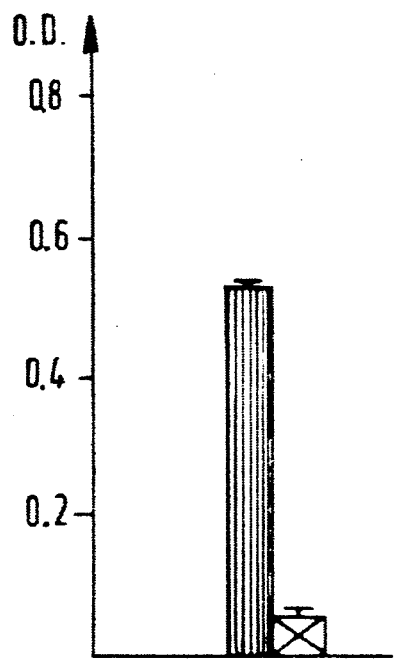
Figure 5:
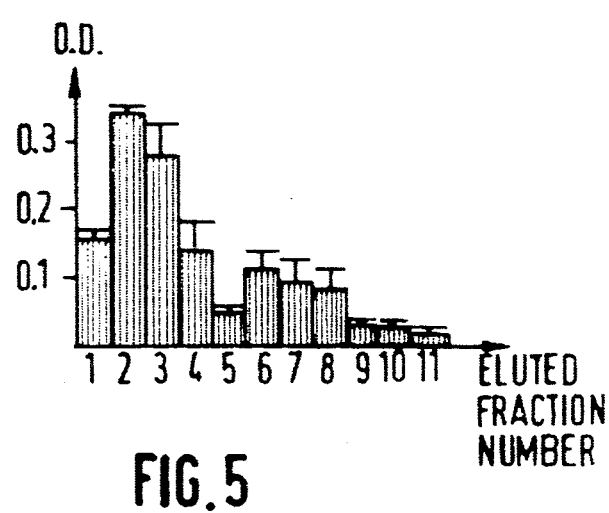

FIGS. 4 and 5 illustrate the results of adsorption experiments on columns of lectin. The experiment was as follows: 500 microliters of normal human serum were deposited twice in succession, at room temperature, in an equivalent volume of agarose coupled to different lectins. In FIG. 4, the lectin in question is that known as Lens Culinaris Agglutinin (or LCA). After the column eluant had been collected, that is to say after everything not retained by the column had been collected, the Fc receptor reactivity was measured using the indirect ELISA technique as described above. The immunoreactivity of the sera before passage through these lectins (solid column) and of the effluent, that is to say of the substances nor retained in the column, was tested, and an almost 90% adsorption of the material according to the invention, representing the Fc receptor immunoreactivity, on these columns is observed. This proves that this material is glycoprotein in nature, and contains glucose and/or mannose residues.

The material adsorbed on this column was then eluted, that is to say detached; this is shown in FIG. 5; this was carried out by applying on the column a solution which enters into competition with the Fc receptor, namely a solution which contains the sugar specific for this lectin. In this instance, the elution solution is a 0.5M α-methyl mannoside solution. In this way, it was possible to elute the Fc receptors from this lectin column; this is shown in FIG. 5. The immunoreactivity, as obtained using the classical sandwich ELISA technique, of the different elution fractions, which are numbered as abscissae, are shown in this figure, and the ordinates indicate the reactivity in ELISA in terms of optical density. It is seen that a classical elution curve, with a peak around the second and third fraction, is indeed obtained. This confirms once more that the Fc receptor according to the invention, as it circulates in the serum, is indeed a glycoprotein.

Figure 6:
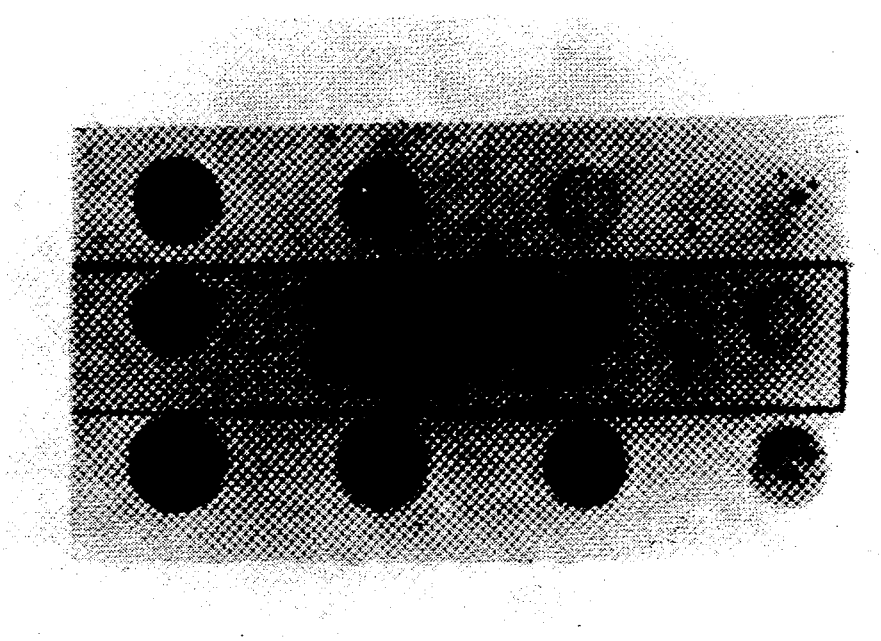

FIG. 6 illustrates the results of a so-called "Dot Blot" experiment. The Dot Blot technique is fully known and referred to in the literature. According to this technique, a cellulose nitrate filter is brought into contact with a solution containing the antigens to be assayed. These antigens are bound to this cellulose nitrate paper by the application of a vacuum on the other side of this porous filter. As a result of the action of the vacuum, the antigen molecules become bound to the cellulose nitrate paper. This paper is then reacted with different antibodies and enables colorimetric reactions to be observed by means of the use of enzyme-labeled antibodies.

In this case, there were three samples, which were tested in parallel:

on the bottom line, the sample is a cell extract, as also described above. This cell extract is tested at four dilutions, from the left to the right of the figure, and shows a classical dilution curve with an immunoreactivity corresponding to the colorimetric reaction observed on the nitrocellulose filter which decreases progressively in proportion to the dilution.

On the middle line, in place of the cell extract, the sample is a serum considered to be positive from the results of the sandwich ELISA technique according to the invention. In this case also, it is found that the test shows a decrease in the optical density obtained, proportional to the dilution of serum which also goes from the left to the right of the figure, hence showing that the reaction in question is equally as specific as that of the sandwich ELISA technique.

On the top line, a serum was tested which was considered to be negative from the results of the sandwich ELISA technique, that is to say, when it is reacted in a first stage with capture by 3G8 on a PVC plate and in the second instance with the system comprising anti-Leu 11b antibody and peroxidase-labeled anti-mouse IgM polyclonal antibody, which usually gave a negative result, the presence was observed, in this negative serum, of material antigenically recognized as an Fc receptor. The only difference here, compared with the sandwich ELISA technique, is, in the first place, that there is no capture stage, and hence no need for this antigen to be recognized by the 3G8 monoclonal antibody, and in the second place, that the antibodies used for visualizing the Fc receptor are not the Leu 11b antibody and anti-mouse IgM antibody but, directly, a rabbit anti-Fc receptor polyclonal antibody, manufactured in the laboratory by immunization of a rabbit with the purified Fc receptor according to the technique described in relation to FIG. 1, and a peroxidase-labeled rabbit anti-immunoglobulin antibody as second antibody.

This shows that some sera considered to be negative by the use of the 3G8/anti-Leu 11b system, are, however, soluble Fc type III receptor carriers. This suggests that an antigen polymorphism exists, some individuals having soluble plasma Fc receptors which are recognized by 3G8/anti-Leu 11b, others having soluble serum Fc receptors which are not recognized by the G8/anti-Leu 11b system.

By means of the assay and purification methods according to the invention, a molecule is made available which can be used in man in the treatment of different conditions:

1—Monoclonal secretions of immunoglobulins, such as multiple myeloma or Kahler's disease.

2—Immune complex disease or diseases accompanied by the presence of tissue or serum immune complexes, such as lupus erythematosus and other autoimmune diseases.

3—Lymphomas and leukemias, in particular Burkitt's lymphoma.

4—Bone marrow or organ (liver, kidney, heart, for example) transplant rejection, for curative or preventive purposes.

5—Acquired immune deficiencies and in particular during infection by HIV virus.

We claim:

1. An isolated low affinity soluble Fc γ R type III receptor, which is a glycoprotein of molecular mass 72,000 to 76,000 daltons and which is immunologically recognized in ELISA and Western Blotting by the monoclonal antibody anti-Leu 11b.

2. A purified low affinity soluble Fc γ R type III receptor which is at least substantially the same as the product obtained by subjecting a biological fluid of human origin to affinity chromatography on a column coupled to a) 3G8 antibodies, b) lectins or c) anti-Fc R receptor polyclonal antibodies, eluting material absorbed on the column and gel filtering thus-obtained eluant, said product having a spectrum, in acrylamide gel electrophoresis under reducing conditions, which has a major band corresponding to a molecular mass of between 72,000 and 76,000 daltons and a plurality of minor bands, the main ones corresponding to molecular masses, respectively, of:
    a) between 64,000 and 68,000 daltons,
    b) between 51,000 and 55,000 daltons,
    c) between 42,000 and 46,000 daltons, and
    d) between 33,000 and 37,000 daltons.

3. A fraction of an Fc γ R type III receptor as claimed in claim 2 which has a molecular mass primarily between 33,000 and 37,000 daltons, as appears in acrylamide gel electrophoresis in the presence of a reducing agent and a detergent.

4. A fraction of an Fc γ R type III receptor as claimed in claim 2 which has a molecular mass primarily between 64,000 and 68,000 daltons, as appears in acrylamide gel electrophoresis in the presence of a reducing agent and a detergent.

5. A fraction of an Fc γ R type III receptor as claimed in claim 2 which has a molecular mass primarily between 51,000 and 55,000 daltons, as appears in acrylamide gel electrophoresis in the presence of a reducing agent and a detergent.

6. A fraction of an Fc γ R type III receptor as claimed in claim 2 which has a molecular mass primarily between 42,000 and 46,000 daltons, as appears in a acrylamide gel electrophoresis in the presence of a reducing agent and a detergent.

7. An Fc γ R type III receptor as claimed in claim 1 or claim 2 or a fraction of either which cross-reacts with a rabbit anti-FcR receptor polyclonal antibody.

8. A fraction of low affinity soluble Fc γ type III receptor, as claimed in claim 1 or claim 2, in combination with one or more other fractions of a low affinity soluble Fc γ type III receptor or CD16, as claimed in claim 1 or claim 2.

9. A receptor as claimed in claim 1 or claim 2, and which is in its native form.

10. A receptor as claimed in claim 2, and which is the same as the product obtained by the process set forth in claim 2.

11. A kit of reagents, which comprises, in at least two separate containers:
    a) a solid support provided with a first antibody which is directed against a conformational epitope of an Fc γ receptor, of claim 1 or 2 to be assayed; the first antibody being a monoclonal antibody, a polyclonal antibody or a fraction of either;
    b) a second antibody which is an anti-Fc receptor recognizing the same category of Fc receptors as the first antibody, but by a completely different epitope; the second antibody being a monoclonal antibody, a polyclonal antibody or a fraction of either;
    c) a third antibody, which has a specific capability of recognizing the second antibody; and
    d) a system for assay of the third antibody.

12. A kit as claimed in claim 11, wherein the solid support is a microtitration plate.

13. A kit as claimed in claim 12, wherein the first antibody is the monoclonal antibody 3G8 the second antibody is a monoclonal antibody consisting of mouse IgM or anti-Leu 11b antibody, and the third antibody is goat anti-mouse IgM polyclonal antibody.

14. The kit as claimed in claim 11, wherein the system for the assay of the third antibody comprises an enzyme conjugated to the said third antibody, a colorimetric substrate associated with the said enzyme and a substance designed to stop the colorimetric reaction.

15. A kit as claimed in claim 14, wherein the enzyme is peroxidase, the substrate associated with the said enzyme is ortho-phenylenediamine in the presence of hydrogen peroxide, and the substance designed to stop the colorimetric reaction is aqueous sulfuric acid solution.

16. A kit as claimed in claim 15, wherein the peroxidase in horseradish peroxidase.

17. A method for identifying or for assay of a soluble form of low affinity Fc γ R type III receptor, which consists essentially of the following steps:
    a) binding, to a solid phase, a first antibody, which is a monoclonal or polyclonal antibody or a fraction of a monoclonal or polyclonal antibody, and which immunologically recognizes a conformational epitope of the Fc γ receptor to be identified or assayed;
    b) washing the solid phase to remove therefrom that portion of the first antibody which is not bound thereto;
    c) incubating a sample, containing the Fc γ receptor to be assayed, in the presence of said solid phase coated with said first antibody;
    d) washing the resulting solid phase to remove therefrom material not specifically bound to the first antibody;
    e) incubating, in the presence of thus-washed solid phase, a second antibody, which is a monoclonal or polyclonal antibody or a fraction of a monoclonal or polyclonal antibody, and which is an anti-Fc receptor antibody which recognizes the same category of Fc receptors as the first antibody, but by a completely different epitope;
    f) washing thus-obtained solid phase to remove therefrom that portion of the second antibody which is not specifically bound thereto;
    g) incubating, in the presence of thus-washed solid phase, a third antibody, which is capable of specifically recognizing said second antibody;
    h) washing thus-obtained solid phase to remove therefrom that portion of the third antibody which is not specifically bound thereto;
    i) assaying the third antibody bound to the thus-washed solid phase; and
    j) deducing therefrom the quantity of Fc receptor initially present in the sample.

18. A method as claimed in claim 17, wherein the first antibody is monoclonal antibody 3G8.

19. A method as claimed in claim 18, wherein the second antibody is a mouse IgM consisting of antibody anti-Leu 11b.

20. A method as claimed in claim 19, wherein the third antibody is a goat anti-mouse IgM polyclonal antibody.

21. A method as claimed in one of claims 17 or 20 wherein a) the third antibody is labeled with an enzyme, b) a colorimetric substrate for the enzyme is reacted with the enzyme in step (i), c) after the colorimetric reaction has stopped, optical density change is measured, and d) the quantity of Fc receptor sought is deduced from the optical density change.

22. A method as claimed in claim 21, wherein the enzyme is horseradish peroxidase, the calorimetric substrate is orthophenylenediamine, in the presence of hydrogen peroxide, and the optical density is measured at 492 nm.

23. A method as claimed in one of claims 17 to 20 or in claim 22, wherein binding in step (a) is conducted at a temperature of about 4° C. for a period of time ranging from 8 to 12 hours.

24. A method as claimed in one of claim 17 to 20 or in claim 22, wherein incubating in each of steps (c), (e) and (g) is effected at room temperature for a period of time ranging from 1 to 4 hours.

* * * * *